United States Patent [19]

Moore et al.

[11] Patent Number: 5,792,431
[45] Date of Patent: Aug. 11, 1998

[54] MULTI-REACTOR SYNTHESIZER AND METHOD FOR COMBINATORIAL CHEMISTRY

[75] Inventors: Michael L. Moore, Media; Dennis Yamashita, King of Prussia, both of Pa.

[73] Assignee: SmithKline Beecham Corporation, King of Prussia, Pa.

[21] Appl. No.: 657,701

[22] Filed: May 30, 1996

[51] Int. Cl.$^6$ .................................................. C08F 2/00
[52] U.S. Cl. .......................... 422/134; 422/116; 422/131; 435/287; 935/88
[58] Field of Search .................................. 422/131, 134, 422/116; 935/88; 435/287, 289

[56] References Cited

U.S. PATENT DOCUMENTS

| | | | |
|---|---|---|---|
| 4,671,941 | 6/1987 | Nina et al. | 422/131 |
| 5,252,296 | 10/1993 | Zuckermann et al. | 422/116 |
| 5,380,495 | 1/1995 | Chang et al. | 422/131 |
| 5,395,594 | 3/1995 | Nokihara et al. | 422/135 |
| 5,503,805 | 4/1996 | Sugarman et al. | 422/131 |
| 5,529,756 | 6/1996 | Brennan | 422/131 |

FOREIGN PATENT DOCUMENTS

| | | |
|---|---|---|
| WO 91/17823 | 11/1991 | WIPO. |
| WO 94/08051 | 4/1994 | WIPO. |

OTHER PUBLICATIONS

Krchnak, Viktor et al., "*Multiple Continuous–Flow Solid–Phase Peptide Synthesis*," Int. J. Peptide Protein Res. 33, 1989, pp. 209–213.

Zuckermann, Ronald N. et al., "*Control of the Zymate Robot with an External Computer*," J. Amer. Chem Soc. 115, 1993, pp. 2529–2531.

Zuckerman, Ronald N. et al., "*Automated Tools for the Production of Non–Natural Molecular Diversity*," Innovation and Perspectives in Solid Phase Synthesis. Collected Papers 3rd International Symposium. Roger Epton, Editor, Mayflower Worldwide Ltd., Brimingham, U.K. 1994, pp. 397–402.

Lowe, Gordon, "*Combinatorial Chemistry*," Chem. Soc. Rev., 1995, pp. 309–317.

Banville et al., "*Automated Technologies for Drug Discovery: Robotic Equimolar Peptide Mixture Synthesis*," Int. Symposium on Lab. Automation and Robotics. 1992.

Brian G. Main et al., "*Automated Chemical Synthesis*," Int. Symposium on Lab Automation and Robotics. 1992, pp. 1–9.

*Primary Examiner*—Christopher Kim
*Attorney, Agent, or Firm*—Dara L. Dinner; Edward T. Lentz

[57] ABSTRACT

Solid phase combinatorial synthesis is carried out in a multi-reactor synthesizer comprising an array of separate reactor cells containing a solid reaction support medium. Subsets of reactor cells are interconnected with one another in a desired pattern, and, in a first reaction step, reagents are circulated through the subsets. After the first reaction step is completed, the reactor cells are rearranged into a new configuration of subsets, and the same, or other, reagents are circulated through the new subsets. The process can be repeated to produce large numbers of compounds differing from one another.

5 Claims, 6 Drawing Sheets

MULTI-REACTOR SYNTHESIZER AND METHOD FOR COMBINATORIAL CHEMISTRY

FIELD OF THE INVENTION

This invention relates to chemical synthesis, and more particularly to an improved apparatus and method for carrying out combinatorial synthesis. The invention has particular utility in drug discovery and in other applications where it is necessary to generate large numbers of related compounds.

BACKGROUND OF THE INVENTION

Combinatorial synthesis is a process for producing large numbers of compounds which can be screened for possible physiological or chemical activity. Typically, it is carried out in a series of successive stages, in each of which an existing molecule is modified chemically.

Various techniques have been devised for combinatorial synthesis.

One such technique is the so-called "split synthesis" method, in which polystyrene beads are provided as solid substrates on which the reactions take place. In the split synthesis method, the beads are divided into a number of groups of equal size. A different monomer is coupled to the beads in each group. The beads are then washed, recombined, thoroughly mixed, and again divided into a number of groups of equal size. Monomers, which may be the same as or different from the original monomers, are coupled to the beads of the new groups. By repeating the process, it is possible to produce large numbers of different compounds. The collection of compounds produced by this method is referred to as a "library."

At each stage of the synthesis, identifier molecules can be attached to the beads. The identifier molecules or "tags" attached to a particular bead uniquely represent the reaction history of the bead, and enable the compound of interest on the bead to be reproduced in quantity after it is determined, by screening for activity, to warrant further investigation.

Another technique for distinguishing compounds is "array synthesis," in which the various compounds are formed at defined locations on a surface. From a knowledge of the reagents added at each location, and the sequence in which they are added, it is possible to determine the reaction history of any compound on the surface.

Robotic systems have been devised to assist in carrying out combinatorial synthesis. For example, robots have been used to automate the synthesis of equimolar peptide mixtures by split synthesis.

On a larger scale, robotic systems have been devised for the automated production of related compounds. These systems typically utilize test tube arrays, or special multi-celled reaction blocks, and include heating or cooling devices to control the temperatures of the tubes or reaction cells, devices for moving the tubes, specialized agitation devices, devices for transferring liquids to and from the tubes or reaction cells, and provisions for maintaining an inert atmosphere.

Peptide synthesis has also been carried out by a continuous flow, solid-phase synthesis method utilizing columns packed with polystyrene-based resin. The flow columns are connected in parallel to provide multiple flow paths, or are connected in series to provide a single flow path. In both cases, complex valving is required to control the flow of various reagents and solvents through the resin-packed columns.

One of the disadvantages of the split synthesis method is that it is carried out on a microscopic scale and requires specialized and expensive techniques to read the molecular tags. The split synthesis method is advantageous in that it is capable of synthesizing very large numbers of compounds. However it is also subject to statistics, in that the splitting and combination of the beads are random, and consequently there is always a statistical probability that not all of the desired variants are present in the library.

Array synthesis is also difficult to carry out in that it requires automated apparatus or masking on a microscopic scale.

The robotic apparatus used for larger scale synthesis is mechanically complex and expensive. The continuous flow, solid-phase synthesis method, used for peptide synthesis, is not well suited for the synthesis of large numbers of related compounds, and requires complex valving to control the flow of the various reagents and other fluids. Both the robotic systems and the continuous flow synthesizers are prone to failure.

Combinatorial synthesis is described in International Patent Application WO 94/08051, published 14 April, 1994; and Lowe, Gordon, *"Combinatorial Chemistry,"* Chem. Soc. Rev., 1995, pp. 309–317.

Apparatus and methods for automated synthesis are described in International Patent Application WO 91/17823, published 28 Nov. 1991; Krchnak, Viktor et al., *"Multiple Continuous-flow Solid-Phase Peptide Synthesis,"* Int. J. Peptide Protein Res. 33, 1989, pp. 209–213; Zuckermann, Ronald N. et al., *"Control of the Zymate Robot with an External Computer. Construction of a Multiple Peptide Synthesizer,"* J. Amer. Chem. Soc., 115, 1993, pp. 2529–2531; and Zuckermann, Ronald N. et al., *"Automated Tools for the Production of Non-Natural Molecular Diversity,"* Innovation and Perspectives in Solid Phase Synthesis, Collected Papers, 3rd International Symposium, Roger Epton, Editor, Mayflower Worldwide Ltd., Birmingham, JK, 1994, pp. 397–402.

SUMMARY OF THE INVENTION

An important object of this invention is to provide an apparatus and method that are capable of carrying out combinatorial synthesis of relatively large numbers of compounds on a macroscopic scale, but which avoid the complexities and high cost associated with conventional robotic synthesizers utilizing test tubes or the like as reactors.

Another object of the invention is to provide a method of synthesis that is analogous to the split synthesis method, but which can be carried out on a macroscopic scale.

Another object of the invention is to provide a simple multi-reactor synthesizer which can be easily maintained and operated in an inert atmosphere.

Still another object of the invention is to provide an apparatus and method for synthesis of relatively large numbers of compounds which are inexpensive, but in which the reaction history of each compound produced can be easily determined with certainty.

A preferred multi-reactor synthesizer in accordance with the invention comprises a set of reactor cells, each reactor cell having an inlet and an outlet, pumping means, preferably a multi-channel pump, for producing separate flow of plural reagents, and means for interconnecting the reactor cells with one another and with the pumping means to establish plural reagent flow paths, with a different reagent in each flow path and with a subset of the reactor cells connected in series in each flow path. The reactor cells are connectible to, and disconnectible from, one another so that reagent flow paths can be established through different subsets of reactor cells connected in series.

To effect continuous flow of reagent, the synthesizer may include means for returning each reagent from the subset of reactor cells through which it flows to the pumping means. If the reagents are continuously recirculated through the reactors, the reactors do not need to be agitated. This simplifies the apparatus, and makes it less likely that the supporting medium in the reactors will be broken up.

In a preferred version of the multi-reactor synthesizer, the reactor cells are held in fixed positions during each reaction step, but each reactor cell is movable from any one fixed position to any other one of the fixed positions so that the reactors can be rearranged to provide different subsets of series-connected reactors.

In a particularly simple synthesizer array in accordance with the invention, the inlet of each reactor cell is directly connectible to the outlet of every other reactor cell. This makes it possible to assemble subsets of reactor cells without interconnecting the cells through separate conduits. Preferably the inlet of each reactor cell is at one end of the cell and its outlet is at its opposite end.

The invention also resides in a novel method of synthesis comprising the steps of: interconnecting reactor cells in a first group of subsets, each subset consisting of plural reactor cells connected in series; causing reagents to flow in series through the reactor cells of each of the subsets of the first group; rearranging the reactor cells in a second group of subsets, each subset of the second group being different as a whole from every subset of the first group; and causing reagents to flow in series through the reactor cells of each of the subsets of the second group. The rearrangement can be effected either by moving reactor cells to change their physical locations in the array, or by redirecting reagent flow while the reactor cells remain in place.

Other objects and advantages of the invention will be apparent from the following detailed description.

DETAILED DESCRIPTION

Figure 1:
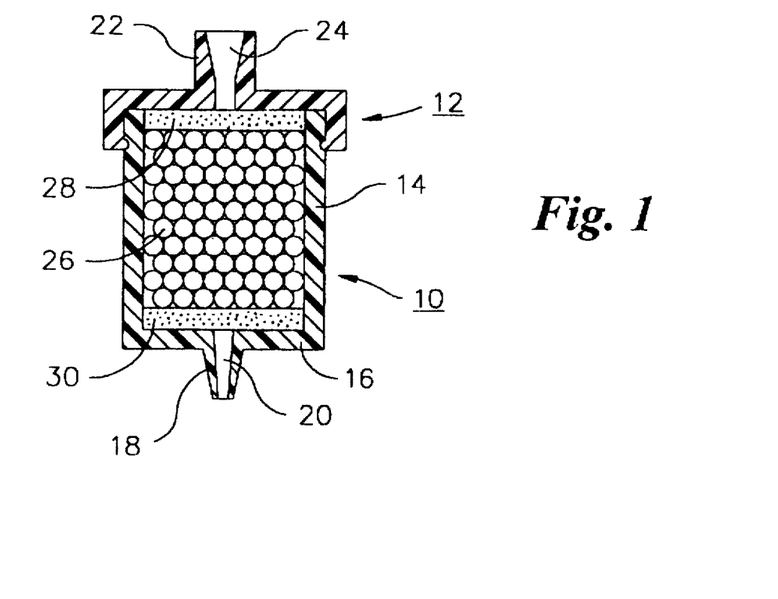
FIG. 1 is an axial cross section through a typical cylindrical reactor cell.

A preferred form of reactor cell is the cylindrical cartridge shown in FIG. 1. The cartridge is molded of polyethylene or similar synthetic resin and comprises a body 10 and a snap-on cover 12. The body comprises a cylindrical side wall 14 and a bottom wall 16 with an externally tapered fitting 18 projecting axially from the center of the bottom wall. The fitting 18 has a central passage 20 leading to the interior of the cartridge body. The cover 12 has an axially projecting fitting 22 with a central passage 24 which is tapered to fit frictionally into the bottom projection of a similar cartridge so that cartridges can be connected together in series.

The cartridge contains an inert supporting medium for immobilizing the compounds being synthesized. In FIG. 1, the supporting medium consists of a mass of porous polystyrene beads 26, held between two porous glass discs 28 and 30.

Figure 2:
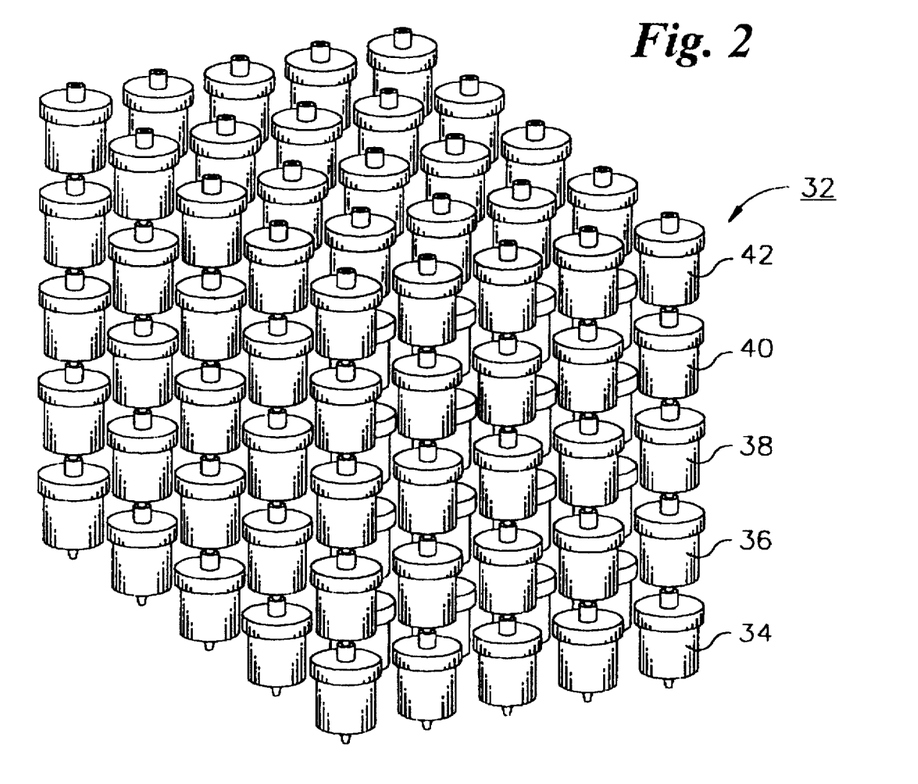
FIG. 2 is a perspective view of set of reactor cartridges arranged in a typical array in accordance with the invention.

In the synthesis process, multiple cells are interconnected in an array, for example as shown in FIG. 2, where the cells are shown in a three-dimensional, 5×5×5 array, consisting of 25 columns, each with five cells connected in series. In column 32, for example, flow of reagent takes place upward through cells 34, 36, 38, 40 and 42.

Alternatively, for some syntheses, the cells can be arranged in two-dimensional array. Furthermore, where desired, the effect of an array of four or more dimensions can be obtained by appropriate rearrangement of cells in successive steps.

The physical arrangement of the columns of cells is not critical, and the 25 columns in FIG. 2, for example can be arranged side by side. Furthermore, although it is desirable to connect the cells directly to one another as in FIG. 2, the cells can be interconnected by other suitable flow passages so that they need not be stacked one on top of another.

Figure 3:
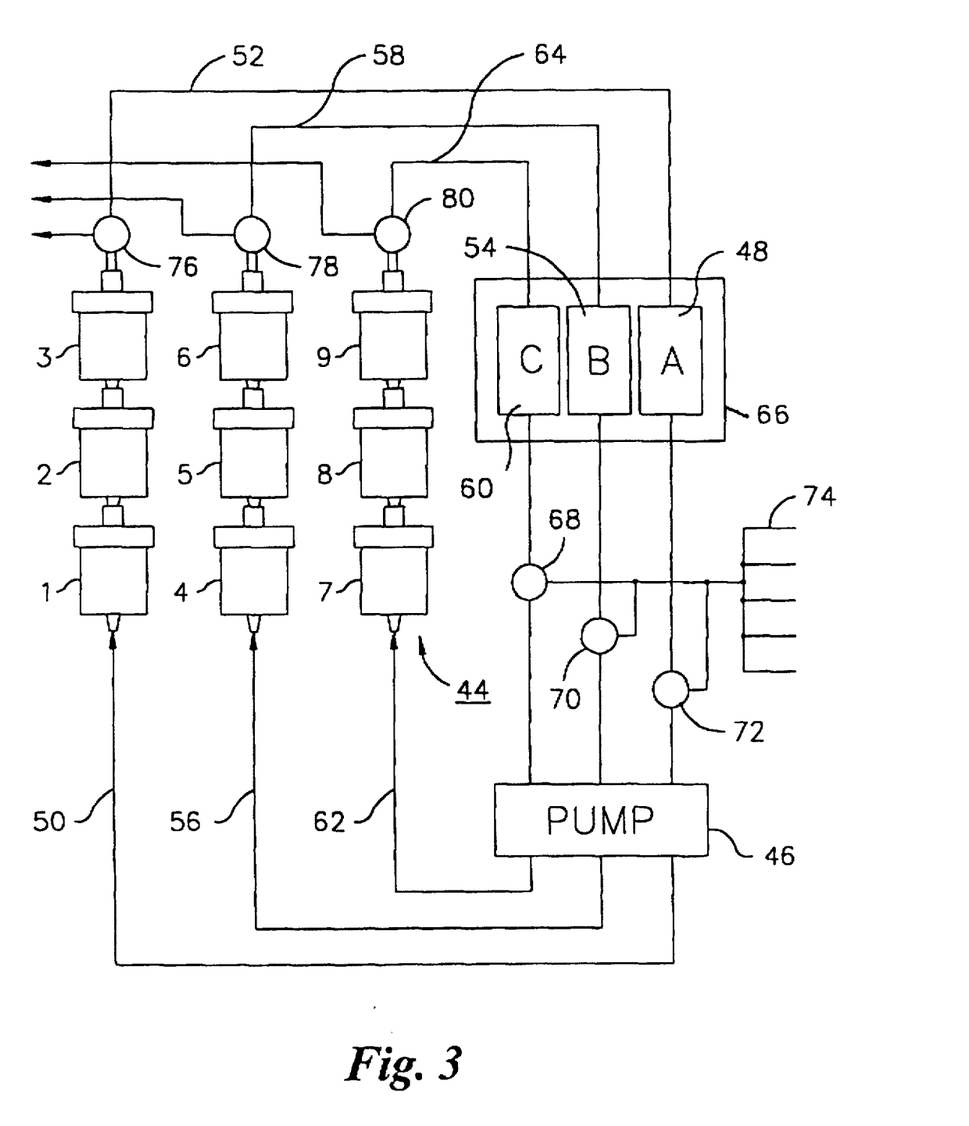
FIG. 3 is a simplified schematic diagram illustrating the flow of reactants through a set of reactor cells.

For simplicity, FIG. 3 shows nine reactor cells in a two-dimensional, 3×3 array 44. A multichannel pump 46 recirculates reagents through the array. Thus, a reagent A, in reservoir 48 is circulated through line 48, reactor cells 1, 2 and 3 and line 50. In a similar manner, reagent B, in reservoir 54 is circulated through line 56, reactor cells 4, 5 and 6 and line 58. Reagent C, in reservoir 60 is circulated through line 62, reactor cells 7, 8 and 9 and line 64. The reagent reservoirs are preferably interchangeable. Thus, other reagents can be substituted readily for reagents A, B and C. For temperature control, the reservoirs are held in a thermostatically controlled block 66, which can be alternatively heated and cooled.

Valves 68, 70 and 72, at the pump inlets, are provided to introduce solvents from bulk solvent feeds 74 to the recirculation lines. Valves 76, 78 and 80 are provided, in lines 52, 58 and 64 respectively, to divert the flow through the reactor array to waste.

As will be apparent, the system of FIG. 3 requires minimal valving. This is advantageous from the standpoint of reliability. The apparatus operates at low pressure, and consequently, no special measures need to be taken in the pumps and fittings to avoid leakage. Because the reagents are continuously recirculated through the reactors, the reactors do not need to be agitated, and the supporting medium is less likely to be broken up. The apparatus is compact and can easily be maintained under an inert atmosphere of nitrogen, argon or similar gas.

Figure 4A:
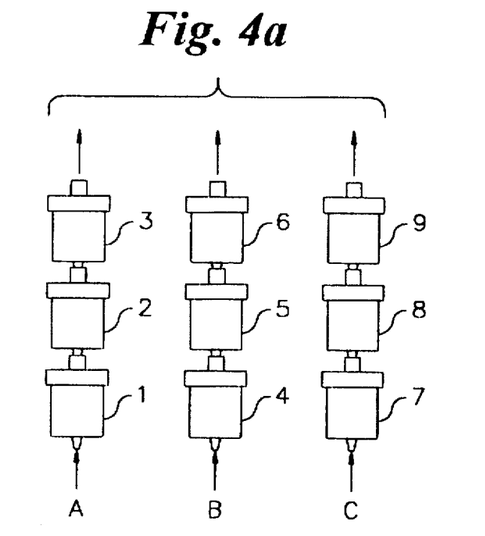
FIGS. 4a, 4b, 4c and 4d are schematic diagrams illustrating the rearrangement of the reactor cells of FIG. 3.
Figure 4B:
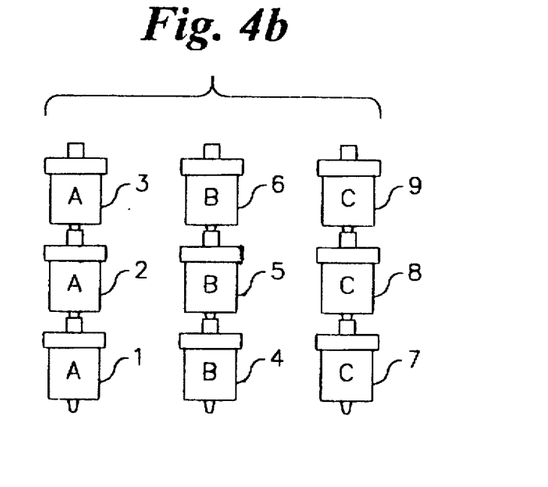

The process of carrying out a simple combinatorial synthesis using the apparatus of FIG. 3 is illustrated in FIGS. 4a–4d. Initially, as shown in FIG. 4a, reagents A, B and C are pumped through the respective columns. As shown in FIG. 4b, each of the reactor cells 1, 2 and 3 in the first column will then contain reagent A. Similarly cells 3, 4 and 5 will contain reagent B and cells 6, 7 and 8 will contain reagent C.

Figure 4C:
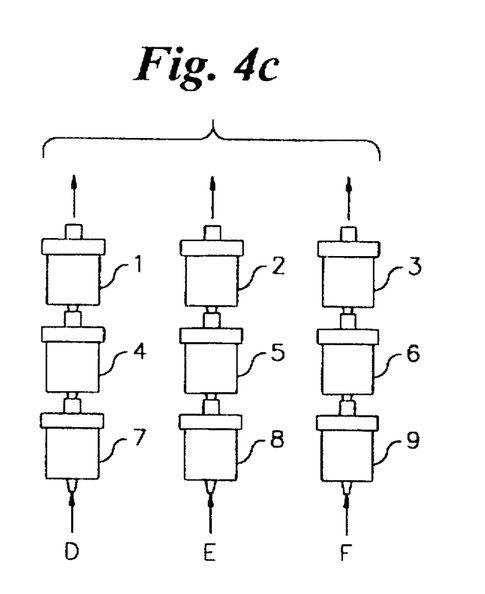
Figure 4D:
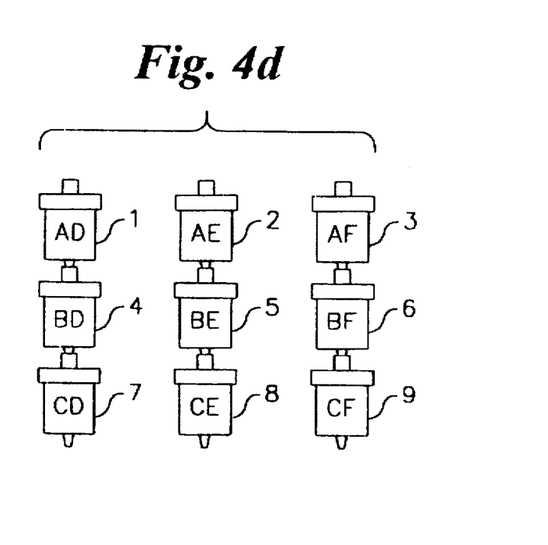

The cells are then rearranged into the configuration depicted in FIG. 4c, with reactor cells 1, 4 and 7 in the first column, cells 2, 5 and 8 in the second column and cells 3, 6 and 9 in the third column. Before resuming operation of the pump 46, the reagent reservoirs may be changed. For example, in the apparatus of FIG. 3, new reagent reservoirs containing reagents D, E and F may be substituted for reservoirs 48, 54 and 60 respectively. When operation of the pump is resumed, reagents D, E and F will flow through the respective columns, and each of the nine cells will contain a different compound, as shown in FIG. 4d. Thus, cell 1 will contain compound AD, cell 2 will contain compound AE, etc.

The choice of reagents and the manner in which the cells are rearranged is merely one example of many possibilities. In the example, all of the possible two component combinations of A, B and C with D, E and F is produced. By carrying out further steps similar to those illustrated in FIGS. 4a–4d, it is possible to synthesize various compounds each having three or more components. By appropriate choice of the number and arrangement of reactors and their rearrangement it is possible, for any given set of reagents, to synthesize all of the possible combinations or selected combinations. By keeping track of the reactors, the researcher can ascertain the reaction history of the compound synthesized in each reactor. It is possible, of course to use the same reagents in two or more steps.

As will be apparent from the preceding description, the reactor cells shown in FIGS. 1 and 2 have the advantage that they can be readily disconnected from one another, rearranged and reconnected with minimal valving. It is possible, however, to realize some of the advantages of this invention by providing an array of reaction cells that remains stationary throughout all or part of the synthesis, and using valving to configure reagent flow paths and thereby effectively achieve reactor cell rearrangement.

Figure 5A:
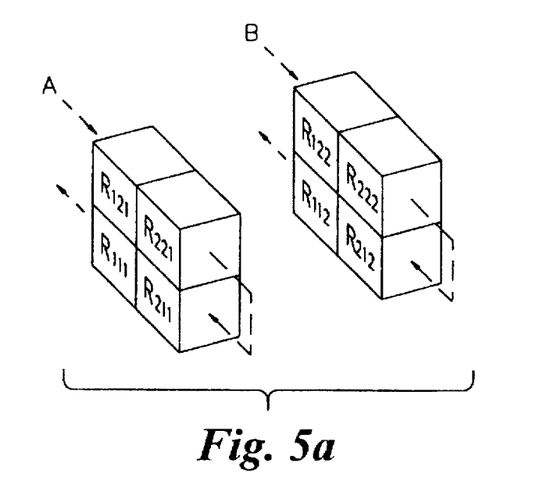
FIGS. 5a, 5b and 5c are schematic diagrams illustrating three successive sets of reagent flow paths through a fixed, 2×2×2 array of reactor cells.
Figure 5B:
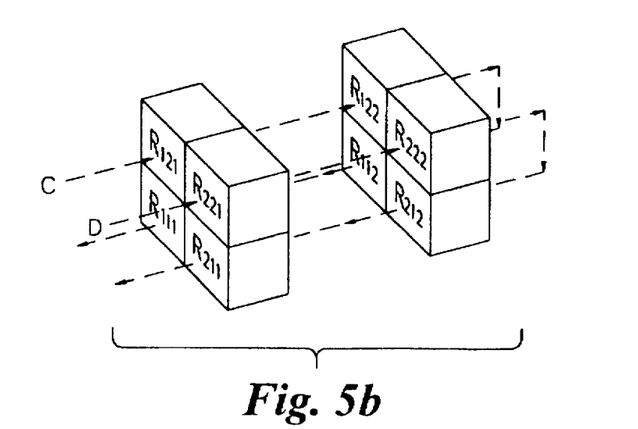
Figure 5C:
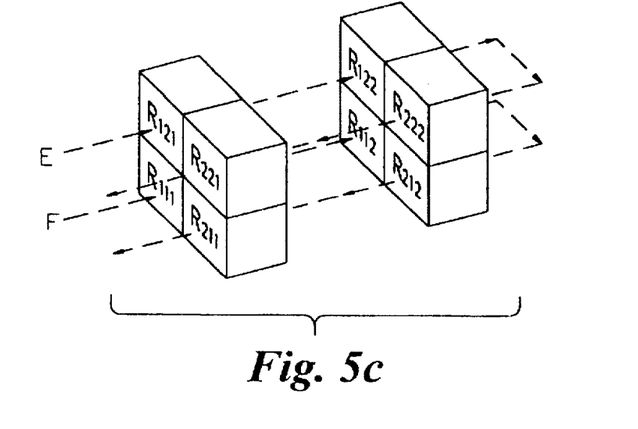

FIGS. 5a, 5b and 5c, for example, show how, using a 2×2×2 array, eight different three-component compounds can be synthesized from six reagents in three steps, using three different flow patterns, without rearranging the reactor cells. In FIG. 5a, reagent A is directed through reactor cells $R_{121}$, $R_{221}$, $R_{211}$, and $R_{111}$ in series. Although not necessarily at the same time, reagent B is directed through reactor cells $R_{122}$, $R_{222}$, $R_{212}$ and $R_{112}$. After the step depicted in FIG. 5a is completed, the valving is set as shown in FIG. 5b, to cause reagent C to flow through cells $R_{121}$, $R_{122}$, $R_{112}$ and $R_{111}$, while reagent D is caused to flow through cells $R_{221}$, $R_{222}$, $R_{212}$ and $R_{211}$. Finally, as shown in FIG. 5c, reagent E is directed through reactor cells $R_{121}$, $R_{122}$, $R_{222}$ and $R_{221}$, and reagent F is directed through cells $R_{111}$, $R_{112}$, $R_{212}$ and $R_{211}$. The result is that each of the reactor cells contains a different compound. Cell $R_{121}$ contains a compound ACE; cell $R_{122}$ contains compound BCE; etc.

Figure 6A:
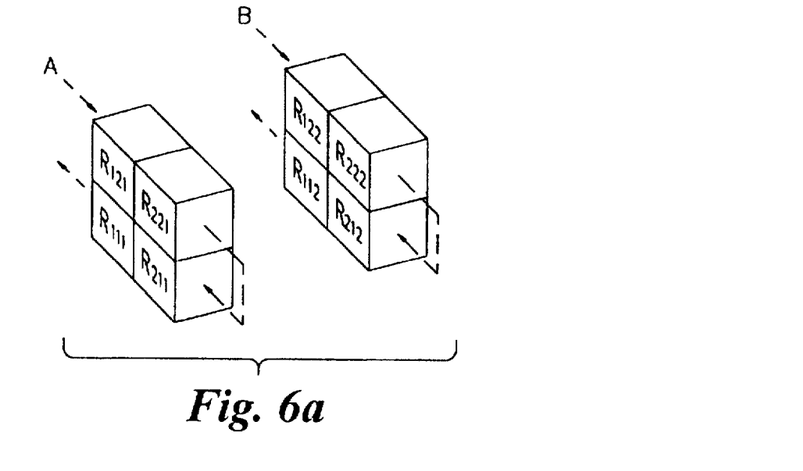
FIGS. 6a, 6b and 6c are schematic diagrams illustrating the rearrangement of a 2×2×2 array of reactor cells to obtain the same effect as obtained in FIGS. 5a, 5b and 5c with a single pair of flow paths.
Figure 6B:
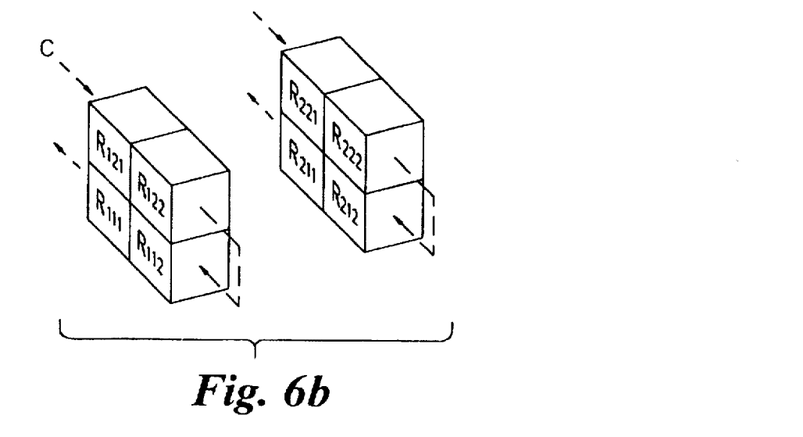
Figure 6C:
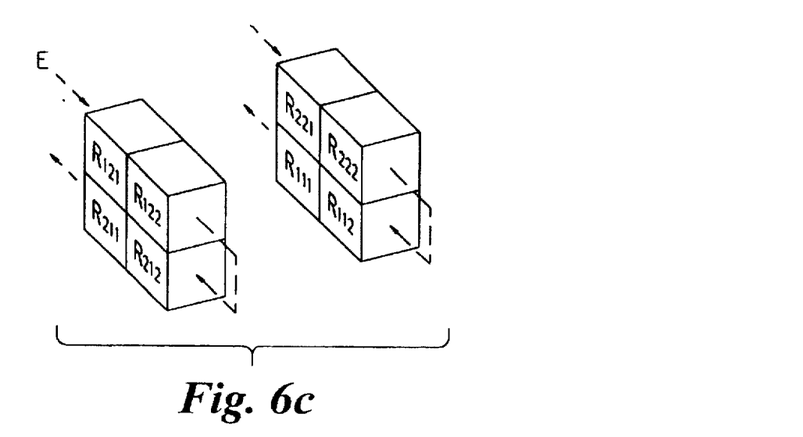

FIGS. 6a, 6b and 6c show how the same result as achieved by the procedure of FIGS. 5a, 5b and 5c is achieved by rearranging the cells without changing the reagent flow paths. FIG. 6a is identical to FIG. 5a. However, to arrive at the cell arrangement in FIG. 6b, cell $R_{122}$ is interchanged with cell $R_{221}$ and cell $R_{112}$ is interchanged with cell $R_{211}$. The other cells remain in their original positions. Reagents C and D are caused to flow through the same paths through which reagents A and B flowed. In proceeding to the cell configuration shown in FIG. 6c, cell $R_{111}$ is interchanged with cell $R_{221}$ and cell $R_{112}$ is interchanged with cell $R_{221}$. Then reagents E and F are caused to flow through the same flow paths through which reagents C and D flowed. As will be apparent from inspection of FIGS. 5a–6c, cell $R_{121}$ contains a compound ACE; cell $R_{122}$ contains compound BCE, etc; and each of the respective cells contains the same compound it would contain if the process of FIGS. 5a–5c were carried out instead.

Figure 7A:
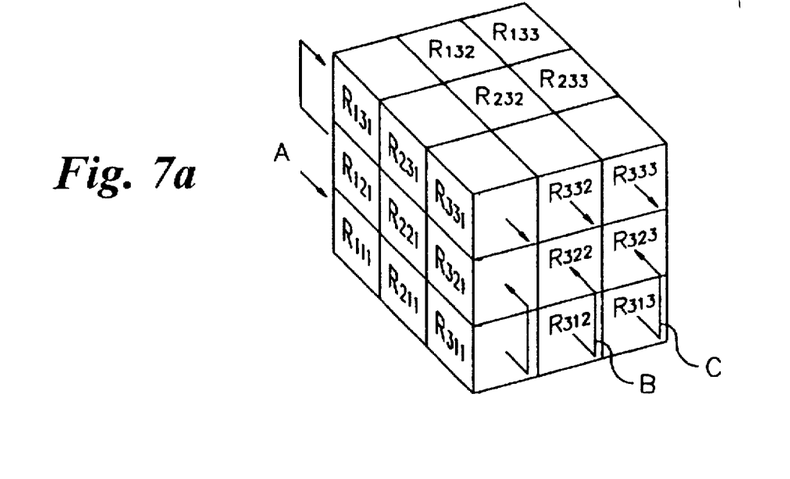
FIGS. 7a, 7b and 7c are schematic diagrams illustrating three successive sets of reagent flow paths through a fixed, 3×3×3 array of reactor cells.
Figure 7B:
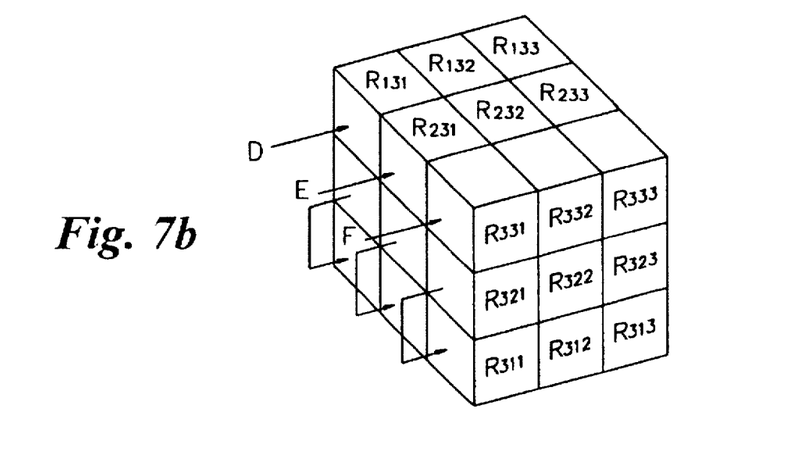
Figure 7C:
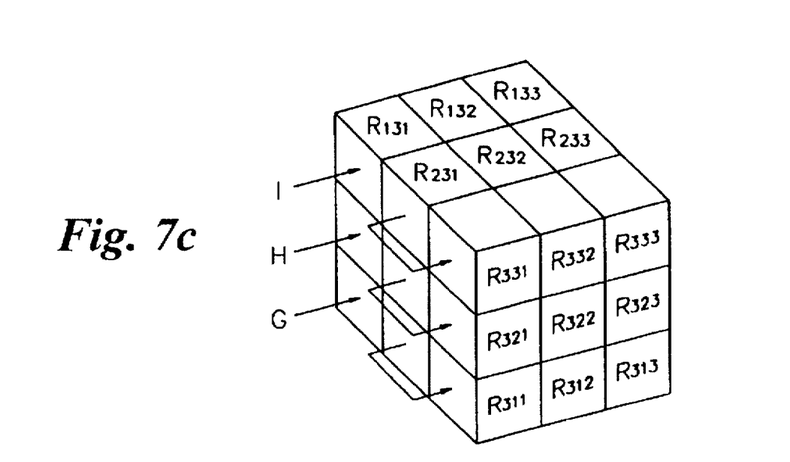

In the procedure depicted in FIGS. 7a–7c, the 27 cells of a 3×3×3 array are maintained in the same relationship while reagent flow paths are changed. In the first step, shown in FIG. 7a, reagents A, B and C are caused to flow respectively through the reactor cells in the layers $R_{xx1}$, $R_{xx2}$ and $R_{xx3}$. In FIG. 7b, reagents C, D and E are caused to flow respectively through the cells in the layers $R_{1xx}$, $R_{2xx}$ and $R_{3xx}$. Finally, in FIG. 7c, reagents G, H and I are caused to flow respectively through the cells in the layers $R_{x1x}$, $R_{x2x}$ and $R_{x3x}$. Here again, when the synthesis is completed, each of the cells contains a different three-component compound. For example, cell $R_{111}$ contains compound ADG; cell $R_{121}$ contains compound ADH; etc.

The process of FIGS. 7a–7c is similar to that of FIGS. 5a–5c, and an equivalent result can be achieved by cell rearrangement in a manner analogous to that depicted in FIGS. 6a–6c.

The invention has been described with reference to comparatively simple multi-reactor arrays, and simple rearrangements of the cells. However, it should be apparent that the apparatus, especially by virtue of its separable and movable reactor cells, lends itself to synthesis of complex, multi-component compounds, using arrays of as many as 1000 or more cells and as many as four or more separate synthesis steps, using numerous reagents.

Thus, the invention has many advantages over prior apparatus and methods for combinatorial synthesis, especially in its structural simplicity, low cost, versatility and ease of use.

Numerous modifications can be made to the apparatus described. For example, the reactor cells can be constructed so that they can be plugged into a cell receiver block at selected positions. Reagent flow can take place through preestablished flow channels in the receiver block, so that the desired flow paths depend on the positions of the cells in the receiver block. Alternatively, groups of reactor cells can be received in multi-cell holders, which are in turn inserted into a receiver block. The holders and receiver block can be constructed so that the flow paths can be changed by moving, e.g. rotating or translating, the holders in the receiver block. Alternatively, the holders can be interchanged with one another to vary the flow paths.

The temperatures of the reactions taking place in the apparatus can be controlled by controlling the temperatures of the circulating reagents. Temperature control can be carried out by the use of one or more thermostatically controlled blocks to hold the reagent reservoirs, or by passing the reagents through suitable heat exchangers. In either case, temperature sensors can be provided to sense the temperature at appropriate points in the reagent circulation paths and provide appropriate feedback signals for temperature control.

Various other modifications can be made to the apparatus and process described without departing from the scope of the invention defined in the following claims.

What is claimed is:

1. A multi-reactor synthesizer for combinatorial chemistry comprising:

a set of reactor cells, each reactor cell having an inlet and an outlet;

pumping means for producing separate flow of plural reagents; and means for interconnecting said reactor cells with one another and with said pumping means to establish plural reagent flow paths, with a different reagent in each of said flow paths and with a subset of said reactor cells in each of said flow paths, each subset consisting of a plurality of said reactor cells connected in series;

in which the reactor cells are connectible to, and disconnectible from, one another so that new plural reagent flow paths can be established through different subsets of said reactor cells, each of said different subsets also consisting of a plurality of said reactor cells connected in series.

2. A multi-reactor synthesizer according to claim 1 including means for returning each reagent from the subset of reactor cells through which the reagent flows to said pumping means, whereby a continuous flow of reagent is effected in each flow path.

3. A multi-reactor synthesizer according to claim 1 including means for holding the reactor cells in fixed positions while reagents are flowing through the reactor cells, and in which each reactor cell is movable from any one of said fixed positions to any other one of said fixed positions, whereby the reactors can be rearranged to provide different subsets of series-connected reactors.

4. A multi-reactor synthesizer according to claim 1 in which the inlet of each reactor cell is directly connectible to the outlet of every other reactor cell, whereby subsets of reactor cells can be assembled by rearranging reactor cells without interconnecting the cells by means of separate conduits.

5. A multi-reactor synthesizer according to claim 1 in which each reactor cell has two opposite ends, in which the inlet of each reactor cell is at one end and the outlet of each reactor cell is at the other end, and in which the inlet of each reactor cell is connectible directly to the outlet of any other reactor cell, whereby subsets of reactor cells can be assembled by rearranging reactor cells without interconnecting the cells by means of separate conduits.

\* \* \* \* \*

UNITED STATES PATENT AND TRADEMARK OFFICE
CERTIFICATE OF CORRECTION

PATENT NO. : 5,792,431
DATED : August 11, 1998
INVENTOR(S) : Michael L. Moore
Dennis Yamashita It is certified that error appears in the above-identified patent and that said Letters Patent is hereby corrected as shown below:

At column 4, line 35, change the second occurrence of "48" to --50--.

At column 4, line 36, change "50" to --52--.

At column 4, line 38, change "56" to --58--.

At column 5, line 64, change the second occurrence of $R_{221}$ to $R_{222}$.

Signed and Sealed this

Twenty-second Day of December, 1998

Attest:

BRUCE LEHMAN

*Attesting Officer*  *Commissioner of Patents and Trademarks*